Figure 1:
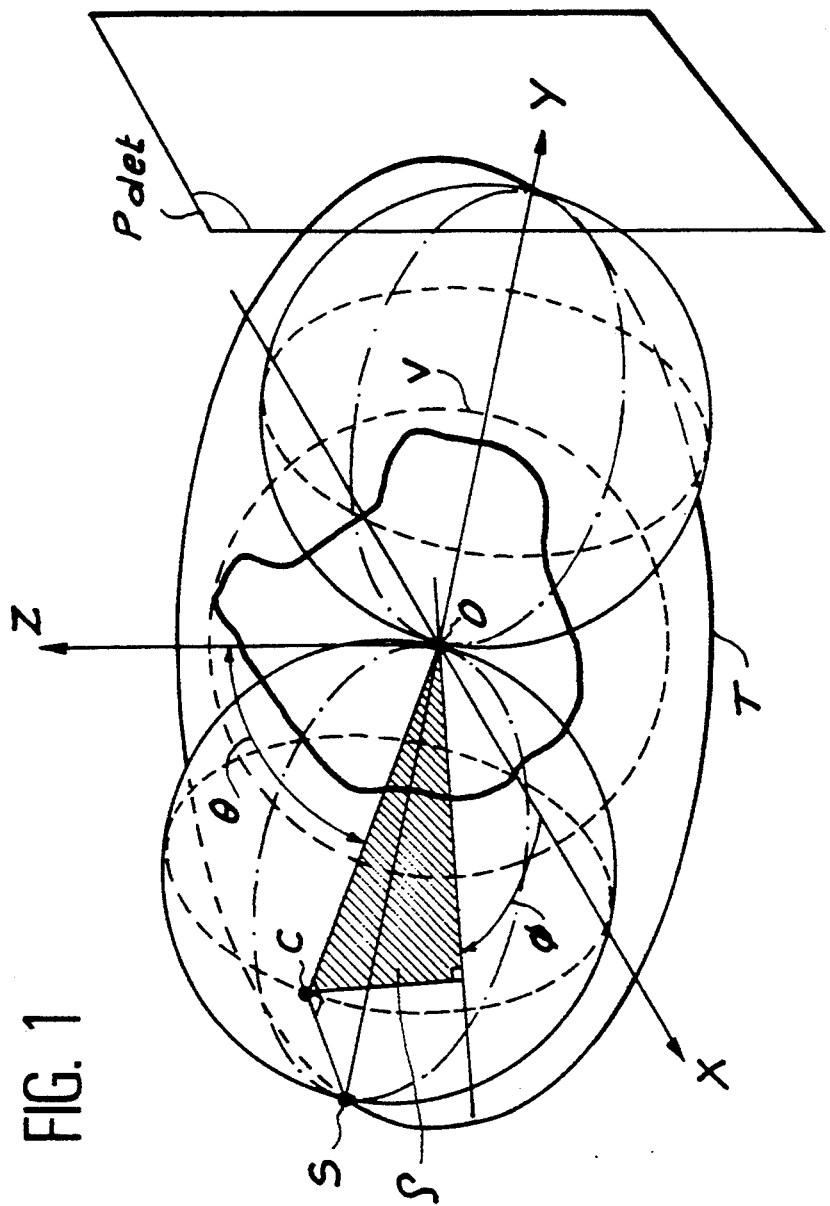

United States Patent [19]
Grangeat et al.

[11] Patent Number: 5,444,792
[45] Date of Patent: Aug. 22, 1995

[54] PROCESS AND APPARATUS FOR THE RECONSTRUCTION OF THREE-DIMENSIONAL IMAGES OF AN OBJECT USING TWO CIRCULAR ACQUISITION PATHS

[75] Inventors: Pierre Grangeat, Saint Ismier; Philippe Rizo, Grenoble; Pascal Sire, Sassenage, all of France

[73] Assignee: Commissariat a l'Energie Atomique, Paris, France

[21] Appl. No.: 259,336

[22] Filed: Jun. 13, 1994

Related U.S. Application Data

[63] Continuation of Ser. No. 788,179, Nov. 5, 1991, abandoned.

[30] Foreign Application Priority Data

Nov. 29, 1990 [FR] France .................. 90 14958

[51] Int. Cl.⁶ .............................................. G06K 9/00
[52] U.S. Cl. ...................... 382/131; 382/276; 364/413.15; 364/413.19
[58] Field of Search .............. 382/6, 54; 364/413.15, 364/413.16, 413.19; 378/4, 17, 901

[56] References Cited

U.S. PATENT DOCUMENTS

| | | | |
|---|---|---|---|
| 4,594,662 | 6/1986 | Devaney | 364/400 |
| 4,977,505 | 12/1990 | Pelizzari et al. | 364/413.19 |
| 5,124,914 | 6/1992 | Grangeat | 364/413.16 |
| 5,160,337 | 11/1992 | Cosman | 606/130 |
| 5,175,773 | 12/1992 | Garreau et al. | 382/6 |
| 5,218,623 | 6/1993 | Toki et al. | 378/4 |

FOREIGN PATENT DOCUMENTS

| | | |
|---|---|---|
| 0292402 | 5/1988 | European Pat. Off. |
| 0379399 | 1/1990 | European Pat. Off. |
| 2088670 | 6/1982 | United Kingdom |

*Primary Examiner*—David K. Moore
*Assistant Examiner*—Andrew W. Johns
*Attorney, Agent, or Firm*—Pearne, Gordon, McCoy & Granger

[57] ABSTRACT

Process for the reconstruction of three-dimensional images of an object. Several measurements are performed by displacing a bidimensional array of sensors, sensitive to a radiation passing through the object or coming from the object in at least two circular paths. The digital method for making it possible to synthesize the informations measured and in particular convert the informations obtained into reference frames linked with the paths in a random reference frame is given. Application to medical imaging or to non-destructive inspection.

12 Claims, 3 Drawing Sheets

PROCESS AND APPARATUS FOR THE RECONSTRUCTION OF THREE-DIMENSIONAL IMAGES OF AN OBJECT USING TWO CIRCULAR ACQUISITION PATHS

This is a continuation of application Ser. No. 07/788,179, filed Nov. 5, 1991, now abandoned.

DESCRIPTION

The invention relates to a process and an apparatus for the reconstruction of three-dimensional images of an object with the aid of a bidimensional array of sensors passing through two circular paths for the acquisition of measurements or, in an equivalent manner, two dimensional arrays of sensors each passing through a circular path. It can also be widened to a random number of paths.

The image of the object is defined by values assumed by a function on each of its points. The function is also a property of a radiation (inter alia gamma or X-rays), which has a conical shape with a focal point and which passes through the object. Each ray is received by one of the sensors of the bidimensional array and consequently represents the sum of the function on all the points of the object belonging to this ray. An appropriate processing of the sums on all the rays for an adequate number of measurements in accordance with different incidences around the object, makes it possible to reconstitute the image of the object.

In practice, there is a limitation to the consideration of a finite number of rays and points of the object in accordance with discretizations or interconnections.

The present invention constitutes an improvement to an earlier-dated invention, described in European patent application EP-A-0 292 402, but use of the present invention can be envisaged in other circumstances or using other mathematical data processing methods.

The methods which can be envisaged more particularly use what is called the Radon transform of the function to be measured, which is defined as the sum of the function on each of the planes, called Radon planes, which pass through the object in question, or preferably the primary derivative of said transform. The contribution of points of these planes not belonging to the object is considered to be non-existent, which applies in the case of a radiation traversing an ambient gaseous medium without being attenuated. Here again, a discretization is carried out so as to only effect the calculations on a finite number of planes.

The primary derivative of the Radon transform is defined as the derivative of the Radon transform as a function of the variable $\rho$ defining the distance from the plane in question to an origin. For each plane, it corresponds to the sum on said plane of the primary derivative of the Radon transform in the direction perpendicular to the plane. The invention described in EP-A-0 292 402 demonstrates that for a plane passing through a position of the focal point of the radiation cone and meeting the bidimensional array of sensors, it is possible to calculate on the basis of measurements the exact value of the primary derivative of the Radon transform on this plane. This calculation, using the formulas described in EP-A-0 292 402 preferably uses a focal point distance correction weighting, two filtering operations corresponding to the calculations of the primary derivatives respectively along the rows and columns of the array of sensors, two summations along the intersection line between the plane to be processed and the bidimensional array of sensors and then a linear combination and standardization of the results. This summation uses the necessary interpolations, because these intersection lines pass between the rows of sensors or intersect them.

Throughout the remainder of the application, the term sum is understood to mean the weighted sum of the measured values (in the case of the Radon transform), as well as the linear combination of the sums of weighted and filtered values (in the case of the primary derivative of the Radon transform) obtained along the rows and columns of the array.

The sum of the function on the points of the Radon planes is easy to obtain, provided that these planes have an intersection with the bidimensional array of sensors and pass through the single focal point aimed at by the sensors. It is sufficient to form the sum of the values measured by each sensor located at the intersection, with the necessary interpolations, because the intersections of the Radon planes pass between the rows of sensors or intersect them. Once the values of the function on the Radon planes have been calculated, there are inversion formulas, described in the aforementioned patent application, which make it possible to arrive at values of the function on the points of the intersection of the corresponding object and the image to be reconstructed.

However, it is always necessary to return to the conditions making it possible to obtain an adequate number of Radon planes to permit a satisfactory description of the object. Each Radon plane can be defined by what is called its characteristic point, i.e. the projection point on said plane of an arbitrarily chosen origin O. This characteristic point, designated C in FIG. 1, can be defined by its spherical coordinates $\rho$, $\phi$ and $\theta$ of radius, longitude and colatitude respectively from the origin O. The Radon plane P passing through the characteristic point C can be defined by the radius $\rho$ and the unitary vector $\bar{n}$ of direction $\overline{OC}$.

The values of the function on the Radon planes can only effectively be calculated for Radon planes intersecting the path covered by the focal point of the radiation. In the case of an attenuation function, this focal point is specifically an X, gamma or similar ray point source. This is the concept which is described in the aforementioned European patent application. The same geometrical conditions exist in emission tomography when the function to be measured is the activity emitted by the body. The focal point then has no physical existence and simply corresponds to the convergence point to which all the collimators used in front of the bidimensional array are directed. In order to obtain an adequate number of Radon planes, several measurements must be performed with different positions of the focal point.

On considering a circular path T traversed by the focal point (or the source) S, the planar array of sensors Pdet passing through the same path as the focal point S or optionally a concentric path of different radius and also assuming that the origin O used for defining the characteristic point C coincides with the centre of the path T. The volume enveloping the characteristic points corresponds to a torus To produced by the rotation of a spherical surface of diameter OS about the rotation axis of the path T. Thus, the Radon planes passing through the focal point S have their characteristic points distributed over the spherical surface of diameter OS, because the angle $\widehat{SCO}$ is a right angle. The torus To is called the characteristic volume of the measurements, which is consequently dependent on the shape of the path T and its position relative to the origin O.

In order to obtain a complete description of the object by processes using the sums of the function on the Radon planes, it is sufficient to be able to have characteristic points belonging to a characteristic volume of the object. This characteristic volume of the object is always included in a sphere V centered on the origin O and which envelops the object M. It is therefore possible to ensure that the image of the object M can be reconstructed if the characteristic volume of the object is included in the characteristic volume of the measurements. In the case of a circular path T, said condition is not unfortunately fulfilled, because a shadow area remains for the characteristic points of the sphere V, which do not belong to the torus To and whose Radon planes do not intersect the path T.

The aforementioned patent application contains the finding that the choice of certain more complicated paths makes it possible to increase the characteristic volume of the measurements for completely filling the characteristic volume of the object. An interesting case is that of the superimposing of two concentric, circular paths belonging to different and e.g. perpendicular planes, because the superimposing of two concentric tori makes it possible to eliminate the shadow area around the origin. A device suitable for such measurements comprises a rail or a slide materializing the path T, on which an X-ray emitter and the bidimensional array of sensors travel in such a way as to always be diametrically opposed and which can tilt about a fixed axis. However, no information was given on the way of effectively reconstructing the image of the object M on the basis of two series of measurements and their synthesis. The present invention specifically relates to a process suitable for the reconstruction of images by means of measurements performed along two circular paths, without any condition being imposed on the geometrical relationships between these paths.

Therefore, the invention relates to a process for the reconstruction of three-dimensional images of an object defined by values assumed by a function on points of the object, the function being a property of a conical radiation having a focal point and passing through the object, in which the function is calculated by means of sums of the function on planes passing through at least one point of the object and defined in an object reference frame having at least two series of measurements, each sum of the function being calculated, on said planes, on the basis of at least one of the series of measurements, each of the series of measurements being carried out with a bidimensional array of radiation sensors oriented towards the focal point and which is displaced around the object on a respective circular path, characterized in that, for each series of measurements, a series of sums of the function is calculated on at least some of the said planes, which are secant or tangential to the path associated with said series of measurements and are then defined in a path reference frame associated with the said path and in that the series of sums of the function are pooled by carrying out calculations in order to be able to define the planes in the object reference frame.

Thus, each series of measurements of the function can firstly be calculated with parameters (incidence of the measurement, distance between the focal point and the array, orientation of the array relative to the axis of the path, etc.) specific to the corresponding series of measurements before assuming homogeneous conditions at the time of pooling the measurements.

Advantageously, the path and object reference frames have an axis in the same direction, which is always possible when there are two paths or, the path reference frames have an axis coinciding with the axis of the corresponding circular path. Preferably, the origin of the path reference frames coincides with the centre of the circle of the path.

It is also advantageous for the groups of coordinates in the path reference frames and the object reference frame to be spherical coordinates and for the reference frame change calculation to have a temporary conversion of spherical coordinates into cartesian coordinates.

It is also possible for the object reference frame to coincide with one of the path reference frames.

An important special case is that of concentric paths.

The object reference frame preferably has an axis in one direction of the interconnection describing the image of the object.

The apparatus according to the invention comprises at least one bidimensional array of sensors, the arrays being displaced around an object to be examined in accordance with at least two circular paths and linked with measurement acquisition and processing means suitable for performing the process according to the invention.

The invention is described in greater detail hereinafter relative to non-limitative embodiments and the attached drawings, wherein show:

FIG. 1, already described, summarizes the geometrical conditions at the source according to the invention.

Figure 2:
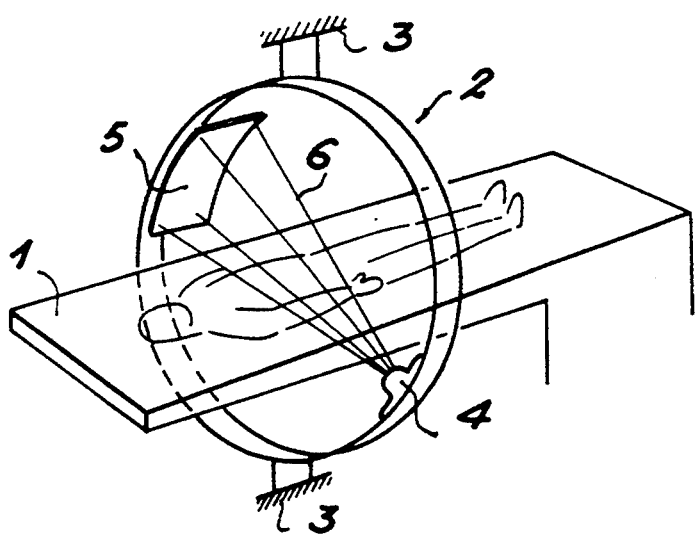

FIG. 2 an apparatus permitting the practical performance of the invention.

Figure 3:
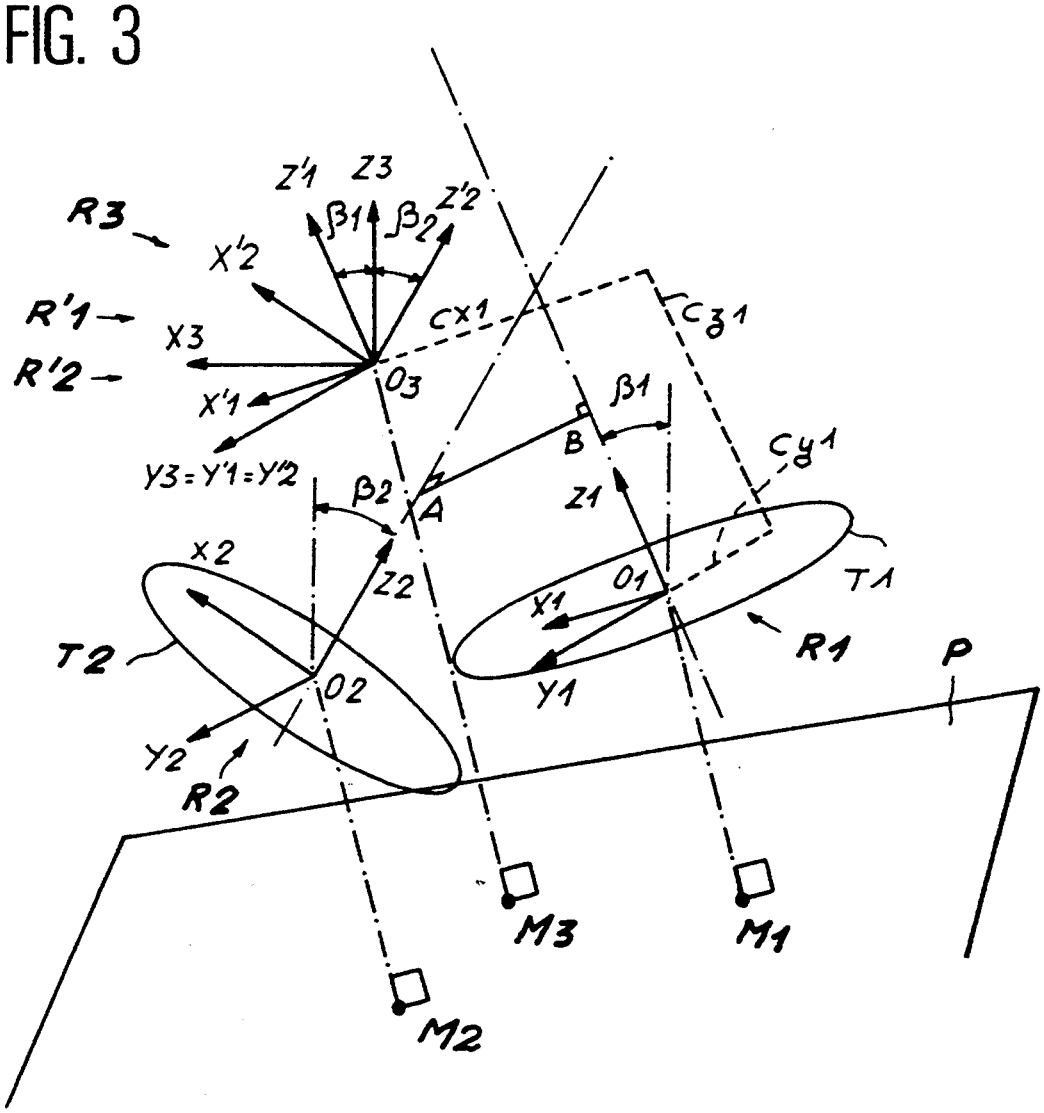

FIG. 3 the geometrical means used.

Figure 4:
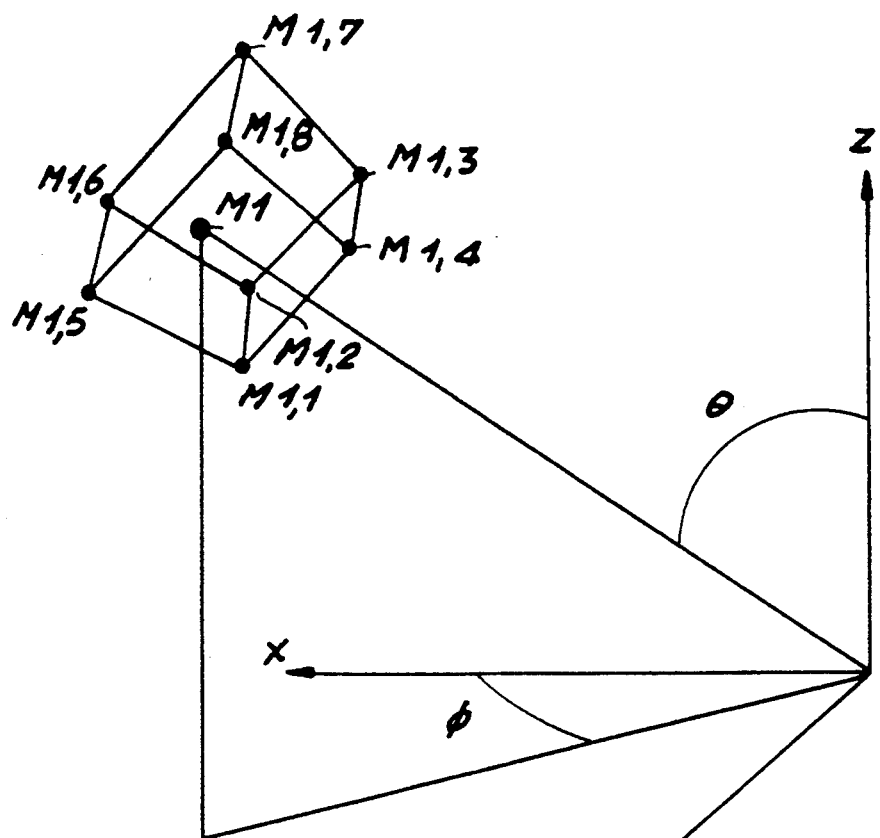

FIG. 4 an explanation of an interpolation stage.

Figure 6:
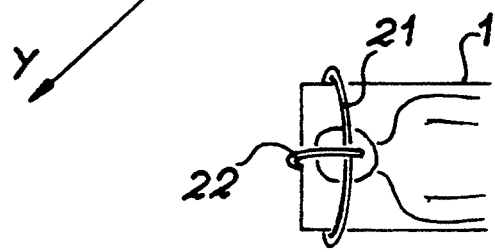
Figure 5:
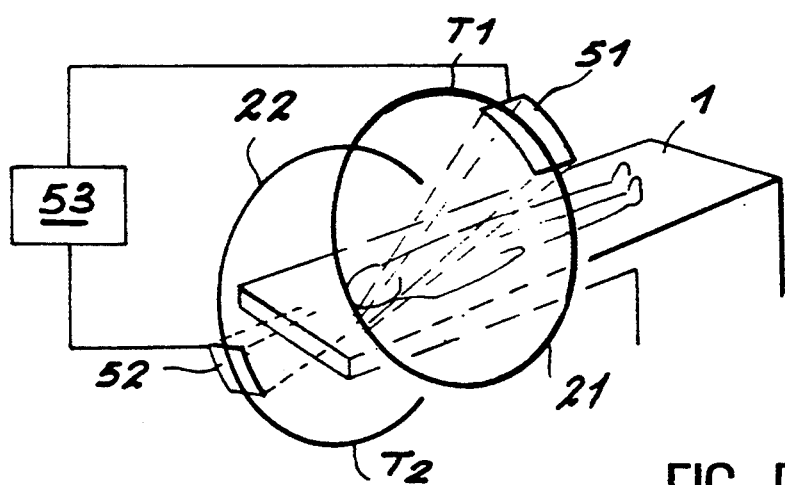

FIGS. 5 and 6 another possible apparatus.

In the case where the object to be examined is a human body irradiated by an external source, the patient can be stretched out on a table 1. A circular rail 2 surrounds the table 1 and can be rotated about a vertical axis with the aid of two hinges 3, which connect it to fixed points of the installation. The circular rail 2 is in fact a rack, which carries in diametrically opposite positions a source 4 emitting a conical beam 6 of X-rays and a screen 5 carrying a bidimensional array of sensors. The source 4 and the screen 5 are moved along the rail 2 under the action of automatically controlled, not shown motors and which operate pinions meshing with the rack. The different circular paths are obtained by the rotation of the rail 2. It is also possible to have a fixed rail and a table 1 movable between predetermined positions. Other means can be used and certain of these are described in the earlier-dated patent application.

FIG. 3 shows the embodiment of the process according to the invention in the most general case where two circular paths T1 and T2 have non-coinciding and non-parallel axes and which have random directions. AB designates the shortest segment for joining these axes. The path reference frames R1 and R2 have as their origin the centres O1 and O2 of the paths T1 and T2, the axes Z1 and Z2 being perpendicular to the respective paths and the axes Y1 and Y2 are parallel. A definition also takes place of an object reference frame R3, in which reconstructions of the image of the object are made. The axis Y3 of this reference frame is parallel to the axes Y1 and Y2 in order to facilitate the calculations. No other condition is required for ensuring the applicability of the following calculations. In practice, the origins O1, O2 and O3 coincide in general and the reference frame R3 is identical to one of the other reference frames R1 or R2. However, as these simplifying cases are not considered here, it is also necessary to define two intermediate reference frames R'1 and R'2 of origin O3 and whose axes are parallel to those of the path reference frames R1 and R2 respectively. $\beta 1$ and $\beta 2$ are the angles between the axis Z3 on the one hand and the axes Z1 or Z'1 and Z2 or Z'2 on the other.

There is a Radon plane P on which the sum calculation has been carried out and for which a reference frame change is necessary for carrying out the pooling or merging of the series of measurements. The orthogonal projections of the three origins O1, O2 and O3 on the plane P are designated M1, M2 and M3. The point M3 is the characteristic point of the Radon plane in the object reference frame R3 and is therefore essential for the inversion calculations of the Radon transform leading to the reconstruction of the object image. However, it lacks significance in the path reference frames R1 and R2, where the same Radon plane P is defined by the characteristic points M1 or M2.

The points M1 to M3 are generally defined by their spherical coordinates, because these coordinates are the most practical for defining regular interconnections on the volumes measured with the aid of circular paths, as well as for defining characteristic points. The conversion into cartesian coordinates only takes place in the final stage in order to define these images of the object by sectional planes. However, a temporary conversion into cartesian coordinates does take place in the process described here. If i is the subscript of one of the reference frames R1,R2 or R3, we obtain the following formulas:

$$X_i = \rho_i \sin(\theta_i) \cos(\phi_i)$$

$$Y_i = \rho_i \sin(\theta_i) \sin(\phi_i)$$

$$Z_i = \rho_i \cos(\theta_i)$$

in order to ensure the correspondence with the cartesian coordinates which will be used in the reference frame change calculations.

The following formulas:

$$X1 = X'1 \cdot \left(1 + \frac{(cx1 \cdot X'1 + cy1 \cdot Y'1 + cz1 \cdot Z'1)}{X'1^2 + Y'1^2 + Z'1^2}\right)$$

$$Y1 = Y'1 \cdot \left(1 + \frac{(cx1 \cdot X'1 + cy1 \cdot Y'1 + cz1 \cdot Z'1)}{X'1^2 + Y'1^2 + Z'1^2}\right)$$

$$Z1 = Z'1 \cdot \left(1 + \frac{(cx1 \cdot X'1 + cy1 \cdot Y'1 + cz1 \cdot Z'1)}{X'1^2 + Y'1^2 + Z'1^2}\right)$$

$X_1' = X_3\cos(\beta_1) + Z_3\sin(\beta_1)Y$
$Y_1' = Y_3$
$Z_1' = -X_3\sin(\beta_1) + Z_3\cos(\beta_1)$ in which cx1, cy1 and cz1 are cartesian coordinates of the origin O3 in the path reference frame R1 make it possible to find the coordinates X1, Y1 and Z1 of the point M1 in the path reference frame R1 as a function of the coordinates X3, Y3 and Z3 of the point M3 in the object reference frame R3. Inverse transformation will also be possible. The calculation for the point M2 is identical to within a subscript change.

This is followed by the calculation of the spherical coordinates $\theta 1$, $\rho 1$ and $\phi 1$ of the point M1 in the reference frame R1 by the following formulas, in which atan signifies arc tangent:

$$\theta_1 = a\tan(\sqrt{X_1^2 + Y_1^2}/Z_1)$$

$$\rho_1 = \sqrt{X_1^2 + Y_1^2 + Z_1^2}$$

if $Z_1 < 0$:

$$\theta_1 = a\tan(\sqrt{X_1^2 + Y_1^2}/(-Z_1))$$

$$\rho_1 = -\sqrt{X_1^2 + Y_1^2 + Z_1^2}$$

if $Z_1 = 0$:

$$\theta_1 = \pi/2$$

$$\rho_1 = \sqrt{X_1^2 + Y_1^2 + Z_1^2}$$

if $Z_1 > 0$:
if $Y_1 > 0$:

$$\phi_1 = a\cos(X_1/\sqrt{X_1^2 + Y_1^2})$$

if $Y_1 < 0$:

$$\phi_1 = 2\pi - a\cos(X_1/\sqrt{X_1^2 + Y_1^2})$$

if $Y_1 = 0$:
if $X_1 > 0$:
$\phi_1 = 0$
if $X_1 < 0$:
$\phi_1 = \pi$
if $X_1 = 0$:
$\phi_1 = 0$.
if $Z_1 \leq 0$:
if $Y_1 > 0$:

$$\phi_1 = \pi + a\cos(X_1/\sqrt{X_1^2 + Y_1^2})$$

if $Y_1 \leq 0$:

$$\phi_1 = \pi - a\cos(X_1/\sqrt{X_1^2 + Y_1^2})$$

if $Y_1 = 0$:
if $X_1 > 0$:
$\phi_1 = \pi$
if $X_1 < 0$:
$\phi_1 = \pi$
if $X_1 = 0$:
$\phi_1 = 0$.

However, the point M1 obtained in this way is not normally a sampling point of the Radon volume corresponding to the first path T1, but is instead an intermediate point between the points of the adopted interconnection. There is then an interpolation of the interconnection in a volume for allocating a value to the point M1 (or $M_i$ in the general case) on the basis of eight surrounding points $M_{i1}$ to $M_{i8}$, whose values of the sum of the function on the Radon plane associated therewith are $V_{ij}$. The interpolation coefficients are $d\rho i$, $d\theta i$ and $d\phi i$ and the sampling spacings are $pe\rho$, $pe\theta$ and $pe\phi$ according to the conventions of FIG. 4. The following formulas are applied:

$$d\rho_i=(\rho_i-\rho_{i,1})/pe\rho=(\rho_i-\rho_{i,2})/pe\rho=(\rho_i-\rho_{i,3})/pe\rho==(\rho_i-\rho_{i,4})/pe\rho$$

$$d\theta_i=(\theta_i-\theta_{i,1})pe\theta=(\theta_i-\theta_{i,2})/pe\theta=(\theta_i-\theta_{i,7})/pe\theta==(\theta_i-\theta_{i,6})/pe\theta$$

$$d\phi_i=(\phi_i-\phi_{i,1})/pe\phi=(\phi_i-\phi_{i,4})/pe\phi=(\phi_i-\phi_{i,6})/pe\phi==(\phi_i-\phi_{i,6})/pe\phi$$

in which $\rho_{ij}$, $\theta_{ij}$ and $\phi_{ij}$ are the spherical coordinates of the point $M_{ij}$, then:

(interpolation on $\rho$)

$$I_{i,1}=Vc_{i,1}(1-d\rho_i)+Vc_{i,5}d\rho_i$$

$$I_{i,2}=Vc_{i,2}(1-d\rho_i)+Vc_{i,6}d\rho_i$$

$$I_{i,3}=Vc_{i,3}(1-d\rho_i)+Vc_{i,7}d\rho_i$$

$$I_{i,4}=Vc_{i,4}(1-d\rho_i)+Vc_{i,8}d\rho_i$$

(interpolation on $\theta$)

$$\pi_{i,1}=I_{i,1}(1-d\theta_i)+I_{i,4}d\theta_i$$

$$\pi_{i,2}=I_{i,2}(1-d\theta_i)+I_{i,3}d\theta_i$$

(interpolation on $\phi$)

$$V_i=\pi_{i,1}(1-d\phi i)+\pi_{i,2}d\phi_i.$$

In the case where the considered function is the primary derivative of the Radon transform, whose sign is dependent on the direction of travel of the rays $\rho$ corresponding to the points M, definition takes place of $V_{ci,j}=V_{i,j}$ if $\rho_{i,j}$ has the same sign as $\rho 3$, if not $V_{ci,j}=-V_{i,j}$. It is pointed out that the spherical coordinates are defined by $-\infty<\rho<+\infty$, $$0<\theta<\frac{\pi}{2} \text{ and } 0<\phi<2\pi.$$

For each of the points of the characteristic volume of the object defined in the object reference frame, the pooling consists, e.g. on an intersection point of the characteristic volumes of each of the paths, of forming a mean of the function sums associated with each path or, for a point belonging exclusively to one of the characteristic volumes of the paths, considerably calculated function sum in the reference frame of said path, said characteristic volumes being defined relative to the origin of the reference frame of the object.

The inversion calculations, e.g. according to the earlier-dated patent application, are carried out when sums of values have been combined for all the points corresponding to the characteristic volume of the object. The same filtering, weighting and back-projection stages are performed. The process can also be used with different modelings or different reference frames and it is possible to use more than two circular paths.

Consideration has more particularly been given to the use of this process for the inversion of the actual Radon transform or its primary derivative. It is possible to proceed in substantially the same way with a Fourier transform of all the radii of the Radon space not intersecting the shadow area, namely for each of the characteristic measurement volumes. The synthesis of the thus transformed measurements in the third reference frame can be carried out with the only change being that the reference frames R1, R2 and R3 have their centres coinciding.

Instead of the Radon transform or its primary derivatives, it is possible to proceed in the same way with the Hilbert transform.

The filtering of the primary derivative could also be carried out before performing the interpolation of FIG. 4, which would make it possible not to determine the orientations. However, it would be necessary to filter the derivatives once for each volume R1 or R2.

If the measurements taken around the paths T1 and T2 do not prove to be adequate, rather than carrying out a rearrangement interpolation as described in the earlier-dated application, where the Radon planes representing the points M1 or M2 are not measured directly, but on the basis of interpolations performed on measurements corresponding to two adjacent positions of the focal point S, it is preferable to incorporate the rearrangement operation into the pooling phase described in the present application, so as to only have to carry out a single interpolation.

As has already been stated, the invention can also be used in emission tomography. It is then more easily possible to accept incomplete circular paths. As shown in FIGS. 5 and 6, another apparatus has a first rail 21 surrounding the table 1 and belonging to a transverse plane with respect to the patient. A second rail 22 is located at one end of the table 1 and belongs to a longitudinal plane of the patient. Unlike previously, it is interrupted in order to provide a passage to the table 1 and to the patient. Such an arrangement is e.g. of interest for examining the brain.

A screen 51 traverses a complete circular path T1 around the rail 21 and a screen 52 traverses a circular arc path T2 around the rail 22. As there is no emission tomography source, the focal point S opposite to the screen 52 on the path T2 can be located on the interruption zone of the rail 22. The measurement acquisition and processing means carry the general reference 53.

The invention can be used for standard medical imaging or the non-destructive inspection of parts.

We claim:

1. A process for reconstructing a three-dimensional image of an object, comprising the steps of:

using at least one two-dimensional array of sensors for acquiring at least two measurement sets of a function at selected points of the object defined by coordinates in an object reference frame, said function, which represents the image of the object, being a property of a radiation viewed by said sensors, wherein the at least one array travels along at least two circular trajectories around the object, the sensors of each of said at least one array of sensors being focused to a respective common focal point beyond the object and at a constant position with respect to said sensors so that each focal point travels along a respective circular focal trajectory and said sensors view a conical space and one trajectory reference frame and one of the measurement sets being associated with each of the focal trajectories;

reconstructing the image of the object from the measurement sets of the image, said image reconstruction including the steps of:

computing for each of the measurement sets, sums of the function over planes (P) of a respective plane set of a plane domain, wherein the planes of the respective plane set are defined by coordinates in the trajectory reference frame associated with the measurement step, the planes of the respective plane set crossing the focal trajectory to which the measurement set is associated and including at least one point of the object, so as to get as many sums as said planes;

merging in an object reference frame the sums provided in the measurement sets in computing, for each of the planes of the plane domain, coordinates defining said plane; and inverting the merged sums in the object reference frame in order to get the reconstructed image of the object.

2. Process for reconstructing three-dimensional images according to claim 1, wherein the trajectory reference frames and object reference frame have an axis with the same direction.

3. Process for reconstructing three-dimensional images according to claim 1, wherein each of the trajectory reference frames has an axis identical to a rotational axis of the trajectory to which the trajectory reference frame is associated.

4. Process for reconstructing three-dimensional images according to claim 1, wherein the object reference frame coincides with one of the trajectory reference frames.

5. Process for reconstructing three-dimensional images according to claim 1, wherein the trajectories are concentric.

6. Process for reconstructing three-dimensional images according to claim 1, wherein the coordinates that define the planes in the trajectory reference frames and the object reference frame are coordinates of characteristic points obtained by projecting respective origin points of said frames on said planes, the characteristic points being generally different for said frames.

7. Process for reconstructing three-dimensional images according to claim 1, further comprising in said gathering step, after the conversions, an averaging of sums associated with planes of the plane domain that have a same position in the object while being defined by different coordinates in different ones of said trajectory reference frames.

8. Process for reconstructing three-dimensional images according to claim 1, wherein the property is an absorption property of the radiation which is produced by a point source placed at each of the focal points.

9. Process for reconstructing three-dimensional images according to claim 1, wherein the property is an emission activity of the radiation which is produced by the object and wherein, for each of the trajectories, the focal point is defined by an intersection of measurement directions of the sensors of the array moving along said trajectory.

10. Process according to claim 1, wherein the coordinates defining the planes of the plane domain are spherical coordinates.

11. Process for reconstructing three-dimensional images according to claim 10, wherein the coordinates in the trajectory reference frames and the object reference frame are spherical coordinates and the gathering of the sums involves a temporary conversion of the spherical coordinates $(\rho, \Theta, \phi)$ in the trajectory reference frames into cartesian coordinates $(X,Y,Z)$, then a conversion of the cartesian coordinates into spherical coordinates in the object reference frame.

12. Process according to claim 1, wherein said at least one array of sensors is moved around the object either by rotating said at least one array of sensors around the object or by rotating the object with respect to said at least one array of sensors which is stationary during each of the trajectories.

* * * * *